(12) United States Patent
Hirai et al.

(10) Patent No.: US 11,399,887 B2
(45) Date of Patent: Aug. 2, 2022

(54) ENERGY TREATMENT INSTRUMENT AND ENERGY TREATMENT SYSTEM

(71) Applicant: OLYMPUS CORPORATION, Hachioji (JP)

(72) Inventors: Yuji Hirai, Sagamihara (JP); Kazuhiro Morisaki, Yokohama (JP); Shunsuke Kuribara, Hino (JP); Satomi Sakao, Hachioji (JP); Satoshi Miyajiri, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 1049 days.

(21) Appl. No.: 16/017,460

(22) Filed: Jun. 25, 2018

(65) Prior Publication Data

US 2018/0303540 A1    Oct. 25, 2018

Related U.S. Application Data

(63) Continuation of application No. PCT/JP2015/086388, filed on Dec. 25, 2015.

(51) Int. Cl.
*A61B 18/14*    (2006.01)
*A61B 17/32*    (2006.01)
*A61B 18/00*    (2006.01)
*A61B 18/08*    (2006.01)

(52) U.S. Cl.
CPC .. *A61B 18/1445* (2013.01); *A61B 17/320092* (2013.01); *A61B 18/085* (2013.01);
(Continued)

(58) Field of Classification Search
CPC .......... A61B 17/320092; A61B 2017/320094; A61B 18/1445; A61B 2018/00345;
(Continued)

(56) References Cited

U.S. PATENT DOCUMENTS 5,693,051 A * 12/1997 Schulze ............ A61B 18/1206
606/41
6,083,223 A * 7/2000 Baker ................ A61B 18/1445
606/49

(Continued)

FOREIGN PATENT DOCUMENTS

JP         2015-204974 A       11/2015

OTHER PUBLICATIONS

Feb. 9, 2016 International Search Report issued in International Patent Application PCT/JP2015/086388.
(Continued)

*Primary Examiner* — Joanne M Hoffman
*Assistant Examiner* — Sean W Collins
(74) *Attorney, Agent, or Firm* — Oliff PLC (57) ABSTRACT

An energy treatment instrument includes a pair of grasping pieces, and the grasping pieces grasp a treated target therebetween by closing relative to each other. At least one of the grasping pieces includes an energy applying portion which treats the treated target by applying treatment energy to the grasped treated target. At least one of the grasping pieces includes a hauler hauling the treated target toward an inside in a width direction of the grasping pieces, when the grasping pieces close relative to each other in a state that the treated target is disposed between the grasping pieces.

6 Claims, 7 Drawing Sheets

(52) U.S. Cl.
CPC ............ *A61B 2017/320069* (2017.08); *A61B 2017/320094* (2017.08); *A61B 2018/0063* (2013.01); *A61B 2018/00345* (2013.01); *A61B 2018/00577* (2013.01); *A61B 2018/00589* (2013.01); *A61B 2018/00702* (2013.01); *A61B 2018/00994* (2013.01)

(58) Field of Classification Search
CPC .. A61B 2018/00589; A61B 2018/0063; A61B 2017/320092; A61B 2017/320069; A61B 18/085; A61B 2018/00577; A61B 2018/00702; A61B 2018/00994
See application file for complete search history.

(56) References Cited

U.S. PATENT DOCUMENTS

| | | | |
|---|---|---|---|
| 2002/0002379 A1 | 1/2002 | Bishop | |
| 2003/0114851 A1 | 6/2003 | Truckai et al. | |
| 2004/0078035 A1* | 4/2004 | Kanehira | A61B 46/23 606/28 |
| 2011/0130757 A1 | 6/2011 | Horlle et al. | |
| 2013/0190760 A1* | 7/2013 | Allen, IV | A61B 18/1442 606/52 |

OTHER PUBLICATIONS

Jun. 26, 2018 International Preliminary Reporton Patentability issued in International Application PCT/JP2015/086388.

* cited by examiner

ENERGY TREATMENT INSTRUMENT AND ENERGY TREATMENT SYSTEM

CROSS-REFERENCE TO RELATED APPLICATIONS

This is a Continuation Application of PCT Application No. PCT/JP2015/086388, filed Dec. 25, 2015, the entire contents of which are incorporated herein by reference.

BACKGROUND OF THE INVENTION

1. Field of the Invention

The present invention relates to an energy treatment instrument configured to treat a treated target by applying treatment energy to the treated target which is grasped between a pair of grasping pieces. Further, the present invention relates to an energy treatment system including this energy treatment instrument.

2. Description of the Related Art

Each of U.S. Patent Application Publication No. 2002/0002379 and U.S. Patent Application Publication No. 2011/0130757 discloses an energy treatment instrument which can grasp a treated target, such as a biological tissue, between a pair of grasping pieces. In each of these energy treatment instruments, at least one of ultrasonic vibration and high-frequency current is applied as treatment energy to the grasped treated target, and thereby the treated target is sealed (coagulated).

BRIEF SUMMARY OF THE INVENTION

According to one aspect of the invention, an energy treatment instrument includes that: a first grasping piece; a second grasping piece openable and closeable relative to the first grasping piece, the second grasping piece being configured to grasp a treated target between the second grasping piece and the first grasping piece by closing relative to the first grasping piece; an energy applying portion provided in at least one of the first grasping piece and the second grasping piece, the energy applying portion being configured to treat the treated target by applying treatment energy to the treated target grasped between the first grasping piece and the second grasping piece; and a hauler provided in at least one of the first grasping piece and the second grasping piece, the hauler being configured to haul the treated target toward an inside in a width direction of the first grasping piece and the second grasping piece, when the first grasping piece and the second grasping piece close relative to each other in a state in which the treated target is disposed between the first grasping piece and the second grasping piece.

According to one another aspect of the invention, an energy treatment instrument includes that: a first grasping piece; a second grasping piece openable and closeable relative to the first grasping piece, the second grasping piece configured to grasp a treated target between the second grasping piece and the first grasping piece by closing relative to the first grasping piece; an energy applying portion provided in at least one of the first grasping piece and the second grasping piece, the energy applying portion being configured to treat the treated target by applying treatment energy to the treated target grasped between the first grasping piece and the second grasping piece; and a hauler provided in at least one of the first grasping piece and the second grasping piece, the hauler being configured to haul the treated target toward an inside in a width direction of the first grasping piece and the second grasping piece, when the first grasping piece and the second grasping piece close relative to each other in a state in which the treated target is disposed between the first grasping piece and the second grasping piece, wherein the first grasping piece includes a first opposed surface which is opposed to the second grasping piece, the first opposed surface includes a first inclined surface and a second inclined surface, the first and second inclined surfaces extending toward a direction of opening of the first grasping piece while extending toward an inside of a width direction in a cross section perpendicular to a longitudinal direction, and the hauler includes a first projection portion projecting toward the first grasping piece, and a second projection portion provided apart from the first projection portion in the width direction, the second projection portion projecting toward the first grasping piece.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
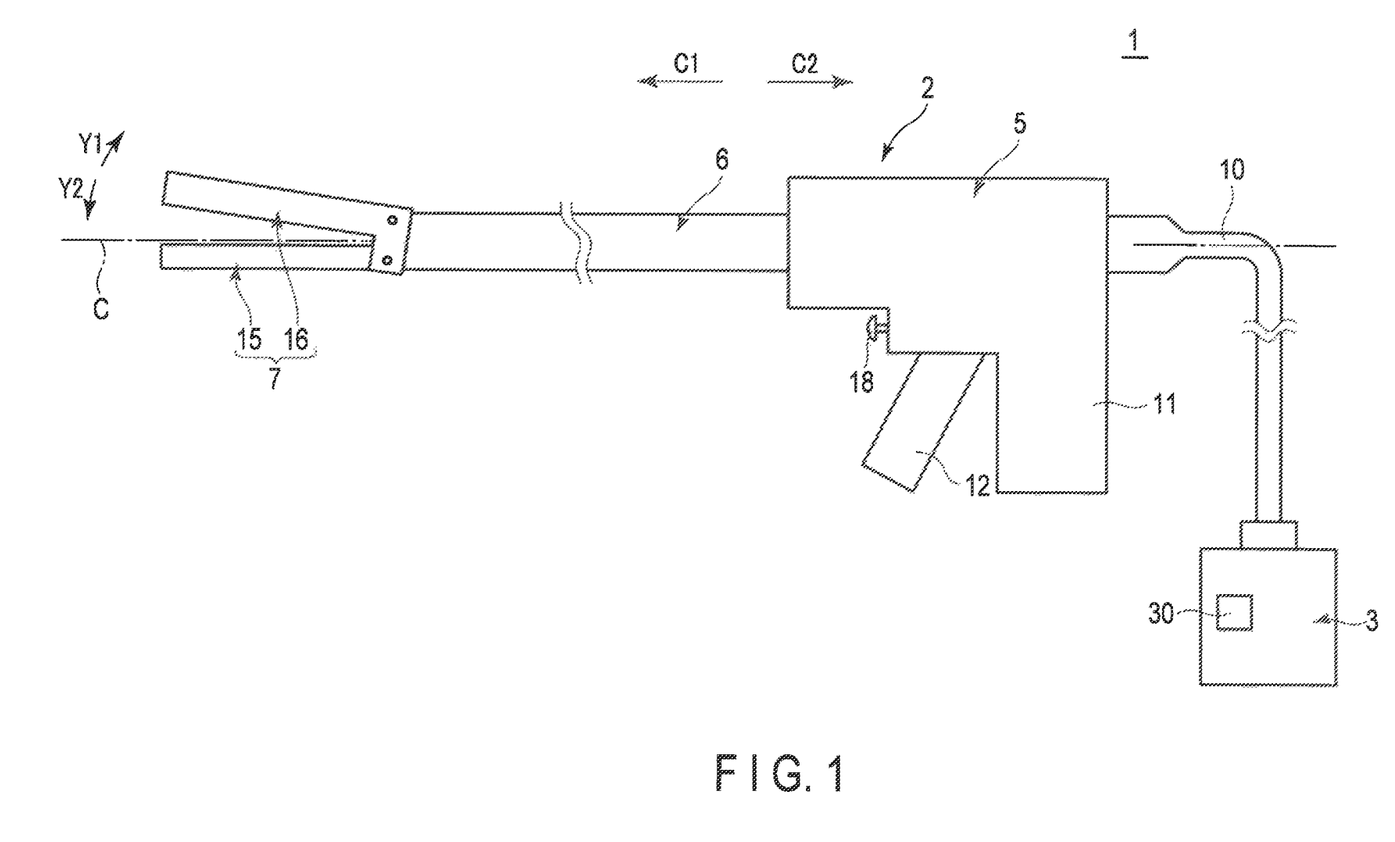
FIG. 1 is a schematic view illustrating a treatment system according to a first embodiment.

A first embodiment of the present invention will be described with reference to FIG. 1 to FIG. 5. FIG. 1 is a view illustrating a treatment system 1 according to the present embodiment. As illustrated in FIG. 1, the treatment system 1 includes an energy treatment instrument 2 and an energy control device 3. The energy treatment instrument 2 has a longitudinal axis C. Here, one side of a direction along the longitudinal axis C is defined as a distal side (arrow C1 side), and a side opposite to the distal side is defined as a proximal side (arrow C2 side).

The energy treatment instrument 2 includes a housing 5 which can be held, a sheath (shaft) 6 which is coupled to the distal side of the housing 5, and an end effector 7 which is provided in a distal portion of the sheath 6. One end of a cable 10 is connected to the housing 5. The other end of the cable 10 is detachably connected to the energy control device 3. In addition, the housing 5 is provided with a grip 11, and a handle 12 is rotatably attached to the housing 5. By the handle 12 rotating relative to the housing 5, the handle 12 opens or closes relative to the grip 11. In the present embodiment, the handle 12 is located on the distal side with respect to the grip 11, and the handle 12 moves substantially in parallel to the longitudinal axis C in the motion of opening or closing relative to the grip 11. However, the embodiment is not limited to this. For instance, in one example, the handle 12 may be located on the proximal side with respect to the grip 11. In another example, the handle 12 may be located on a side opposite to the grip 11 with respect to the longitudinal axis C, and a movement direction in the motion of opening or closing relative to the grip 11 may cross (may be substantially perpendicular to) the longitudinal axis C.

The sheath 6 extends along the longitudinal axis C. In addition, the end effector 7 includes a first grasping piece 15, and a second grasping piece 16 which can open or close relative to the first grasping piece 15. The handle 12 and end effector 7 are coupled via a movable member (not shown) which extends along the longitudinal axis C in the inside of the sheath 6. The handle 12 is opened or closed relative to the grip 11. Thereby, the movable member moves along the longitudinal axis C relative to the sheath 6 and housing 5, and the pair of grasping pieces 15 and 16 open or close relative to each other. Accordingly, the handle 12 functions as an opening and closing operation input section to which an operation of opening or closing the grasping pieces 15 and 16 relative to each other is input. By the grasping pieces 15 and 16 closing relative to each other, a biological tissue such as a blood vessel can be grasped as a treated target between the grasping pieces 15 and 16. The opening and closing directions (directions of arrow Y1 and arrow Y2) of the grasping pieces 15 and 16 cross (are substantially perpendicular to) the longitudinal axis C. In addition, in the state in which the grasping pieces 15 and 16 are closed relative to each other, each of the grasping pieces 15 and 16 extends substantially parallel to the longitudinal axis C.

It should suffice if the end effector 7 is configured such that the paired grasping pieces 15 and 16 open or close relative to each other in accordance with an opening operation or a closing operation of the handle 12. For instance, in one example, one of the grasping pieces 15 and 16 is formed integral with the sheath 6 or fixed to the sheath 6, and the other of the grasping pieces 15 and 16 is rotatably attached to the distal portion of the sheath 6. In another example, both the grasping pieces 15 and 16 are rotatably attached to the distal portion of the sheath 6. In still another example, a rod member (not shown) is inserted through the sheath 6, and one of the grasping pieces 15 and 16 is formed by a projecting portion of the rod member (probe), which projects from the sheath 6 toward the distal side. In addition, the other of the grasping pieces 15 and 16 is rotatably attached to the distal portion of the sheath 6. Besides, in one example, a rotary operation knob (not shown) may be attached to the housing 5. In this case, by rotating the rotary operation knob around the longitudinal axis C, the sheath 6 and end effector 7 rotate, together with the rotary operation knob, around the longitudinal axis C relative to the housing 5. Thereby, the angular position of the end effector 7 around the longitudinal axis C is adjusted.

The energy control device 3 includes an electric power source, a conversion circuit which converts electric power supplied from the electric power source to electric energy which is supplied to the energy treatment instrument 2, a processor (controller) or the like including a CPU (Central Processing Unit) or an ASIC (Application Specific Integrated Circuit), and a storage medium such as a memory. In addition, an operation button 18 functioning as an energy operation input section is attached to the housing 5 of the energy treatment instrument 2. By detecting an operation input in the operation button 18, the energy control device 3 outputs electric energy which is supplied to the energy treatment instrument 2. Incidentally, the energy operation input section, to which an operation of outputting electric energy from the energy control device 3 is input, is not limited to the operation button 18. In one example, in place of the operation button 18 or in addition to the operation button 18, a footswitch or the like, which is separate from the energy treatment instrument 2, may be provided as the energy operation input section.

Figure 2:
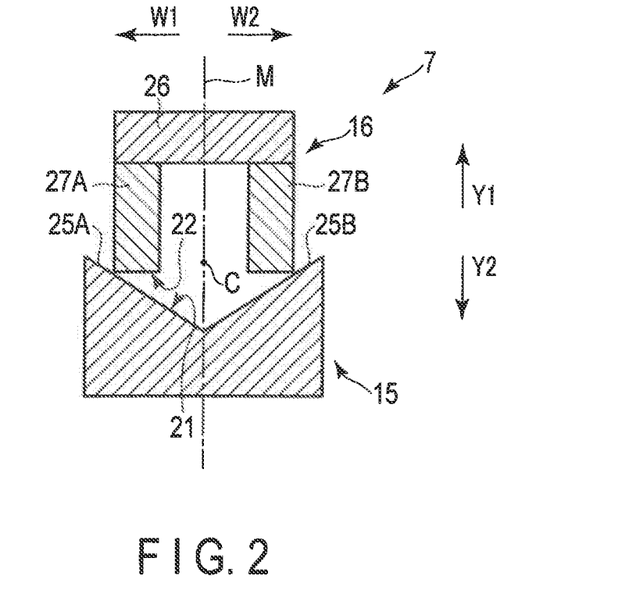
FIG. 2 is a cross-sectional view which schematically illustrates an end effector according to one example of the first embodiment by a cross section substantially perpendicular to a longitudinal axis.
Figure 3:
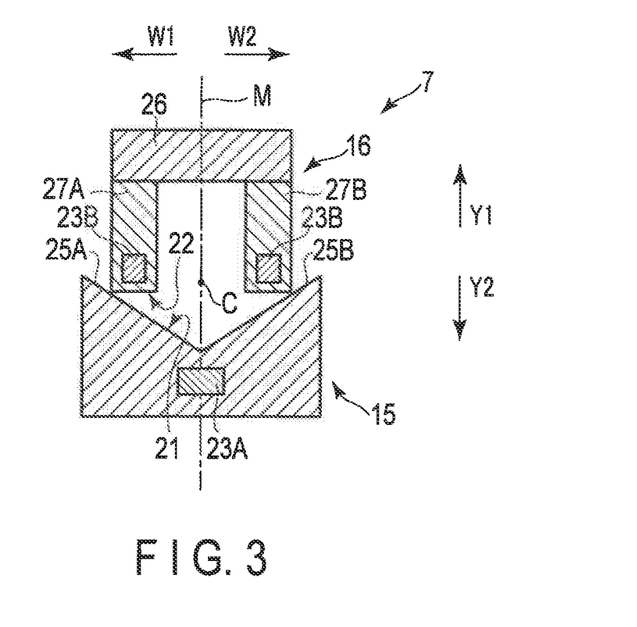
FIG. 3 is a cross-sectional view which schematically illustrates an end effector according to another example of the first embodiment by a cross section substantially perpendicular to the longitudinal axis.

FIG. 2 illustrates an end effector 7 in one example in a cross section substantially perpendicular to the longitudinal axis C, and FIG. 3 illustrates an end effector 7 in another example in a cross section substantially perpendicular to the longitudinal axis C. As illustrated in FIG. 2 and FIG. 3, the first grasping piece 15 includes a first opposed surface 21 which is opposed to the second grasping piece 16. In addition, the second grasping piece 16 includes a second opposed surface 22 which is opposed to the first grasping piece 15 (first opposed surface 21). Here, a direction, which crosses (is substantially perpendicular to) the longitudinal axis in the end effector 7 and crosses (is substantially perpendicular to) the direction of opening and closing of the grasping pieces 15 and 16, is defined as a width direction (directions of arrow W1 and arrow W2) of the end effector 7 (first grasping piece 15 and second grasping piece 16).

In the end effector 7, treatment energy is applied from at least one of the first opposed surface 21 and second opposed surface 22 to a treated target grasped between the grasping pieces 15 and 16, and the treated target is sealed (coagulated). Specifically, at least one of the first grasping piece 15 and second grasping piece 16 is provided with an energy applying portion (21; 22; 21, 22) which applies treatment energy to the grasped treated target. Therefore, at least one of the first opposed surface 21 and second opposed surface 22 is functioned as an energy applying surface.

In one example, ultrasonic vibration is applied as treatment energy to the treated target. In this case, an ultrasonic transducer (not shown) is provided in the inside of the housing 5, and a rod member (not shown) is inserted through the sheath 6 as a vibration transmitting member. In addition, in the inside of the housing 5, the rod member is connected to the distal side of the ultrasonic transducer, and the first grasping piece 15 is formed by the projecting portion of the rod member, which projects from the sheath 6 toward the distal side. In this example, electric energy (AC electric power) that is output from the energy control device 3 is supplied to the ultrasonic transducer, and thereby ultrasonic vibration is generated in the ultrasonic transducer. By the generated ultrasonic vibration being transmitted from the proximal side toward distal side in the rod member (vibration transmitting member), the rod member including the first grasping piece 15 vibrates. By the rod member vibrating in the state in which the treated target is grasped between the grasping pieces 15 and 16, the ultrasonic vibration is applied to the treated target as treatment energy via the first opposed surface (energy applying portion) of the first grasping piece 15. At this time, frictional heat by vibration is generated between the grasped treated target and the first grasping piece 15, and the treated target is, while being cut and opened, sealed (coagulated) by the generated frictional heat.

In another example, high-frequency current is applied to the treated target as treatment energy. In this case, electrodes are provided on the first grasping piece 15 and second grasping piece 16, respectively, and electric energy (high-frequency electric power) that is output from the energy control device is supplied to these electrodes. By the electric energy being supplied to these electrodes in the state in which the treated target is grasped between the grasping pieces 15 and 16, the high-frequency current flows through the treated target between the electrodes. Specifically, the high-frequency current is applied as treatment energy to the grasped treated target through the first opposed surface 21 of the first grasping piece 15 and the second opposed surface 22 of the second grasping piece 16, which are the energy applying portions (energy applying surfaces). By the high-frequency current flowing through the treated target, heat is generated in the treated target, and the treated target is coagulated by the generated heat. In this example, an abutment portion, which is formed of electrically insulating material, is provided on at least one of the first opposed surface 21 and second opposed surface 22. Thereby, a contact between the electrodes is prevented, and the occurrence of short-circuit is prevented in the electrical path of high-frequency current flowing through the treated target.

Besides, in one example, in addition to the above-described electrodes, a cutter (not shown) or the like, which is movable along the longitudinal axis C relative to the grasping pieces 15 and 16, may be provided. In this case, by moving the cutter, the grasped treated target is cut and opened. At the same time, by passing high-frequency current through the treated target as described above, the treated target is sealed (inosculated).

In another example (see FIG. 3), each of the grasping pieces 15 and 16 is provided with a heat generating body (corresponding one of 23A and 23B). In this example, by electric energy (DC electric power or AC electric power) being supplied from the energy control device 3 to each of the heat generating bodies 23A and 23B, heat is generated in each heat generating body 32A, 23B. By the heat being generated in each heat generating body 23A, 23B in the state in which the treated target is grasped between the grasping pieces 15 and 16, the heat generated by the heat generating body 23A is applied to the treated target through the first opposed surface (energy applying portion) 21, and the heat generated by the heat generating body 23B is applied to the treated target through the second opposed surface (energy applying portion) 22. By the heat generated by each of the heat generating bodies 23A and 23B being applied as treatment energy to the treated target, the treated target is cut and opened and, at the same time, coagulated. Incidentally, the heat generating bodies (23A, 23B) do not need to be provided on both grasping pieces 15 and 16. In one example, the heat generating body (23A; 23B) may be provided on only one of the grasping pieces 15 and 16.

Furthermore, a plurality of treatment energies, such as ultrasonic vibration, high-frequency current and heat generated by the heat generating body (23A, 23B; 23A; 23B), may be simultaneously applied to the grasped treated target. In one example, ultrasonic vibration and high-frequency current are simultaneously applied to the treated target as treatment energies. In this case, at the same time as ultrasonic vibration is generated by the supply of electric energy from the energy control device 3 to the above-described ultrasonic transducer, electric energy is supplied from the energy control device 3 to the electrode of each of the grasping pieces 15 and 16. In another example, high-frequency current and heat generated by the heat generating body (23A, 23B; 23A; 23B) are simultaneously applied to as treatment energies to the treated target. In this case, at the same time as the heat is generated by the supply of electric energy from the energy control device 3 to the above-described heat generating body (23A, 23B; 23A; 23B), the electric energy is supplied from the energy control device 3 to the electrode of each of the grasping pieces 15 and 16.

As illustrated in FIG. 2 and FIG. 3, in the present embodiment, inclined surfaces 25A and 25B are provided on the first opposed surface 21 of the first grasping piece 15 that is one of the grasping pieces 15 and 16. Each of the inclined surfaces 25A and 25B extends toward the side (arrow Y2 side) toward which the first grasping piece 15 opens, while extending toward the inside in the width direction of the first grasping piece 15. Specifically, each of the inclined surfaces 25A and 25B inclines so that, while approaching a central position M of the end effector 7 in the width direction, each of the inclined surfaces 25A and 25B extends toward the side toward which the first grasping piece 15 opens. In addition, the inclined surfaces 25A and 25B are continuous at or near the central position M with respect to the width direction of the end effector 7 (grasping pieces 15 and 16).

The second grasping piece 16, which is the other of the grasping pieces 15 and 16, includes a base portion 26 and projection portions (arms) 27A and 27B projecting from the base portion 26 toward the first grasping piece 15 (the one of the grasping pieces 15 and 16). The projection portions 27A and 27B are distant from each other in the width direction of the end effector 7. In the present embodiment, the projection portion 27A is located on one side (arrow W1 side) of the width direction of the end effector 7 with respect to the central position M of the end effector 7 in the width direction, and the projection portion 27B is located on the other side (arrow W2 side) of the width direction of the end effector 7 with respect to the central position M.

By the grasping pieces 15 and 16 closing relative to each other, the projection portion 27A of the second grasping piece 16 is pushed by reaction force from the inclined surface 25A of the first grasping piece 15, and/or slides along the inclined surface 25A. Thereby, the projection portion 27A bends toward the inside (the side toward the central position M) in the width direction of the end effector 7. In addition, by the grasping pieces 15 and 16 closing relative to each other, the projection portion 27B of the second grasping piece 16 is pushed by reaction force from the inclined surface 25B of the first grasping piece 15, and/or slides along the inclined surface 25B. Thereby, the projection portion 27B bends toward the inside (the side toward the central position M) with respect to the width direction of the end effector 7.

Figure 4:
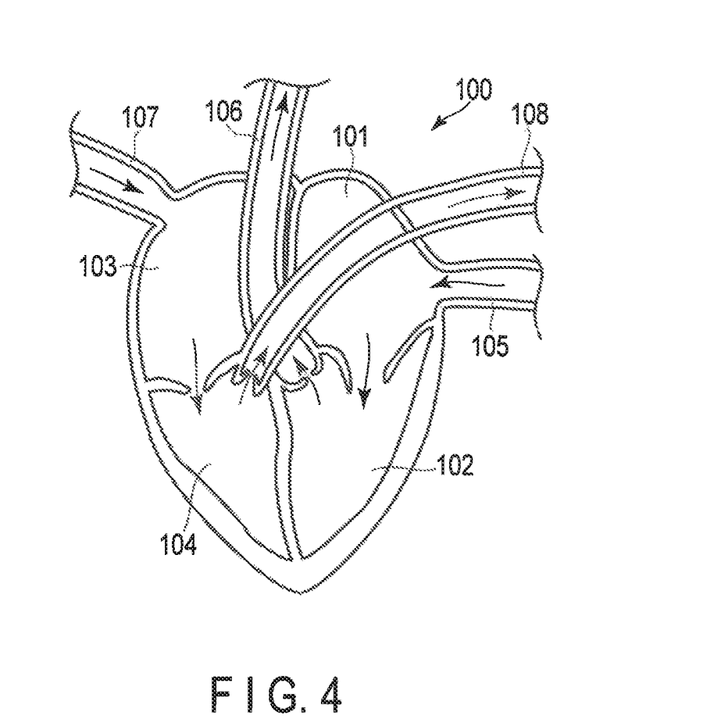
FIG. 4 is a schematic view illustrating a structure of the heart and its peripheral region.

Next, the function and advantageous effects of the energy treatment instrument 2 will be described. In the present embodiment, the energy treatment instrument 2 is used mainly for a treatment of sealing (coagulating), while cutting and opening, a blood vessel of the pulmonary circulation system. FIG. 4 is a schematic view illustrating the structure of the heart 100 and its peripheral region. As illustrated in FIG. 4, the heart 100 includes the left atrium 101, left ventricle 102, right atrium 103 and right ventricle 104. The pulmonary vein 105 extends from the left atrium 101, and the aorta 106 extends from the left ventricle 102. In addition, the vena cava 107 extends from the right atrium 103, and the pulmonary artery 108 extends from the right ventricle 104. A circulation path, by which blood is guided from the left ventricle 102 to the entire body through the aorta 106 and the blood returns from the entire body to the right atrium 103 through the vena cava 107, is referred to as "body circulation". Besides, a circulation path, by which blood is guided from the right ventricle 104 to the lungs through the pulmonary artery 108 and the blood returns from the lungs to the left atrium 101 through the pulmonary vein 105, is referred to as "pulmonary circulation".

When a blood vessel of a pulmonary circulation system is treated, the end effector 7 is inserted into the thorax, and the end effector 7 is moved to a state in which the blood vessel is located between the grasping pieces 15 and 16. In addition, in the state in which the blood vessel that is the treated target is disposed between the grasping pieces 15 and 16, the handle 12 is closed relative to the grip 11. Thereby, the grasping pieces 15 and 16 close relative to each other, and the blood vessel is grasped. In the state in which the blood vessel is grasped between the grasping pieces 15 and 16, the running direction (extending direction) of the blood vessel crosses the direction along the longitudinal axis C, and crosses the direction of opening and closing of the grasping pieces 15 and 16. Further, in the state in which the blood vessel is grasped between the grasping pieces 15 and 16, an operation input is performed by the operation button 18. Thereby, as described above, at least one of ultrasonic vibration, high-frequency current and heat is applied as treatment energy to the blood vessel, and the blood vessel is cut and opened and, at the same time, sealed (coagulated).

Figure 5:
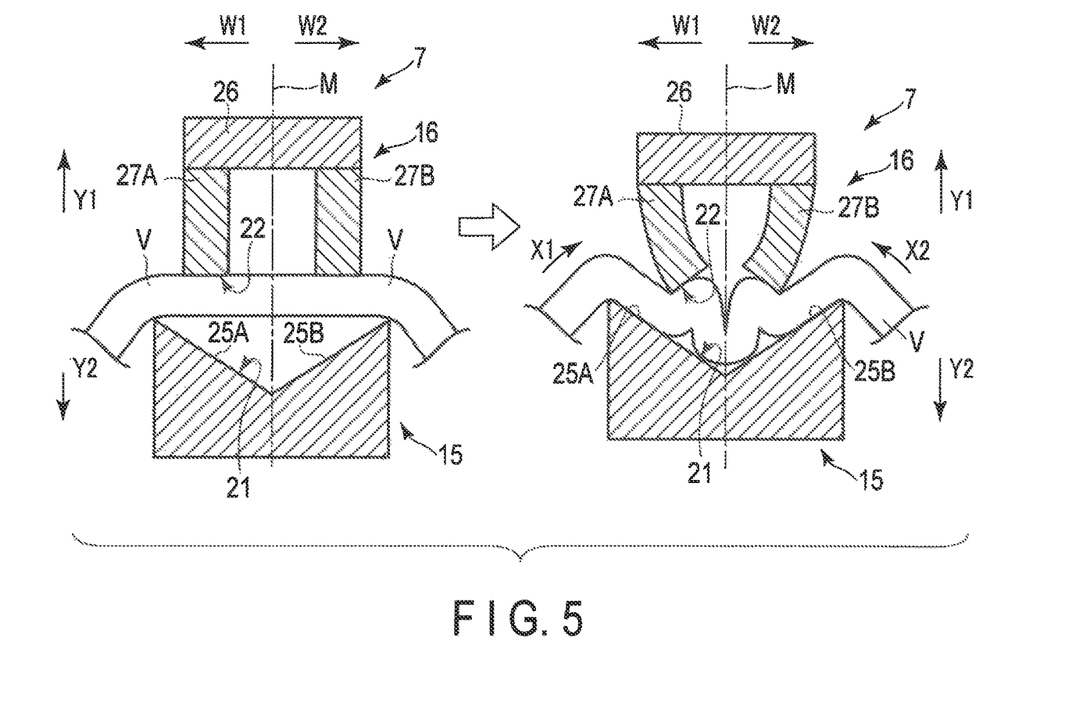
FIG. 5 is a schematic view for describing an operation of grasping a blood vessel between the grasping pieces according to the first embodiment.

FIG. 5 is a view for describing an operation of grasping a blood vessel V between the grasping pieces 15 and 16. As described above, in the present embodiment, by the grasping pieces 15 and 16 closing relative to each other, each of the projection portions (projections) 27A and 27B of the second grasping piece 16 is pushed and/or slid by the corresponding inclined surface (corresponding one of 25A and 25B), and bends toward the inside (toward the central position M) with respect to the width direction of the end effector 7. Thus, as illustrated in FIG. 5, when the grasping pieces 15 and 16 close relative to each other in the state in which the blood vessel (treated target) V is disposed between the grasping pieces 15 and 16, each of the projection portions 27A and 27B bends, and thereby each of the projection portions 27A and 27B pushes the blood vessel V toward the inside in the width direction of the end effector 7. Thereby, as indicated by arrows X1 and X2, the blood vessel V is hauled toward the central position M with respect to the width direction of the end effector 7 (grasping piece 15, 16). At this time, the blood vessel V is hauled from both sides in the width direction of the end effector 7. Thereby, the blood vessel V is hauled to a region between the grasping pieces 15 and 16 (between the opposed surfaces 21 and 22) from the region located on the outside relative to the grasping pieces 15 and 16 in the width direction of the end effector 7. By the blood vessel V being hauled toward the inside with respect to the width direction of the end effector 7, the length (volume) of that portion in the blood vessel V, which is clamped between the grasping pieces 15 and 16 (between the opposed surfaces 21 and 22), increases. As described above, in the present embodiment, the projection portions 27A and 27B are actuated as haul portions (hauler), when the grasping pieces 15 and 16 close relative each other in the state in which the blood vessel (treated target) V is disposed between the grasping pieces 15 and 16. Specifically, when the grasping pieces 15 and 16 close relative to each other, the projection portions 27A and 27B haul the treated target, which is grasped between the grasping pieces 15 and 16, toward the inside in the width direction of the end effector 7.

Here, it is known that the blood vessel of the pulmonary circulation system has a smaller lumen wall thickness than the blood vessel of the body circulation system. Thus, in the blood vessel of the pulmonary circulation system, the amount of a biological high polymer, which is gelatinized in sealing treatment (inosculation treatment), in a cross section perpendicular to the extending direction becomes smaller. In this embodiment, when the grasping pieces 15 and 16 close relative to each other, the projection portions 27A and 27B that are the haul portions (hauler) are actuated, and the blood vessel is hauled toward the inside in the width direction of the end effector 7. Thus, even in the case of the blood vessel of the pulmonary circulation system in which the amount of the biological high polymer in the cross section perpendicular to the extending direction is small, the length (volume) of the portion clamped between the grasping pieces 15 and 16 increases in the range of the width between the projection portions 27A and 27B. Therefore, a sufficient amount of biological high polymer is secured in the entirety of the portion clamped between the grasping pieces 15 and 16 in the blood vessel. Since the amount of biological high polymer, which is gelatinized in the portion clamped between the grasping portions 15 and 16, is secured, the sealing performance (coagulation performance) is improved even in the case of the blood vessel of the pulmonary circulation system. Thereby, the treatment performance is improved in a treatment of coagulating, while cutting and opening, the blood vessel of the pulmonary circulation system.

In addition, it is known that a greater tensile force tends to act on the blood vessel of the pulmonary circulation system, when grasped between the grasping pieces 15 and 16, than on the blood vessel of the body circulation system. If a large tensile force acts on the blood vessel, the blood vessel tends to easily move to the outside with respect to the width direction of the end effector 7 in the state in which treatment energy is being applied to the blood vessel. In the present embodiment, as described above, when the grasping pieces 15 and 16 close relative to each other, the blood vessel is hauled toward the inside in the width direction of the end effector 7 by the projection portions 27A and 27B that are the haul portions. Thus, in this embodiment, even if a large tensile force acts on the blood vessel, the movement of the blood vessel toward the outside in the width direction of the end effector 7 can effectively be prevented.

As described above, in the present embodiment, the energy treatment instrument 2, which is suitable for the treatment of sealing (while cutting and opening) the blood vessel of the pulmonary circulation system, can be provided. Specifically, this embodiment can provide the energy treatment instrument 2 which can exhibit a proper treatment performance even when the compositions of biological tissues are different, for example, as in a case in which the compositions of biological tissues are different between the blood vessel of the pulmonary circulation system and the blood vessel of the body circulation system.

Modification of the First Embodiment

In one modification, the energy control device 3 may be provided with a setter 30 (see FIG. 1) which sets actuation states of the projection portions 27A and 27B that are the haul portions. The setter 30 is a knob, a button, a touch panel, etc. In the present modification, based on the setting in the setter 30, the actuation state of the projection portions 27A and 27B is switched. For example, based on the setting in the setter 30, switching is performed as to whether the projection portions 27A and 27B are to be actuated or not.

Figure 6:
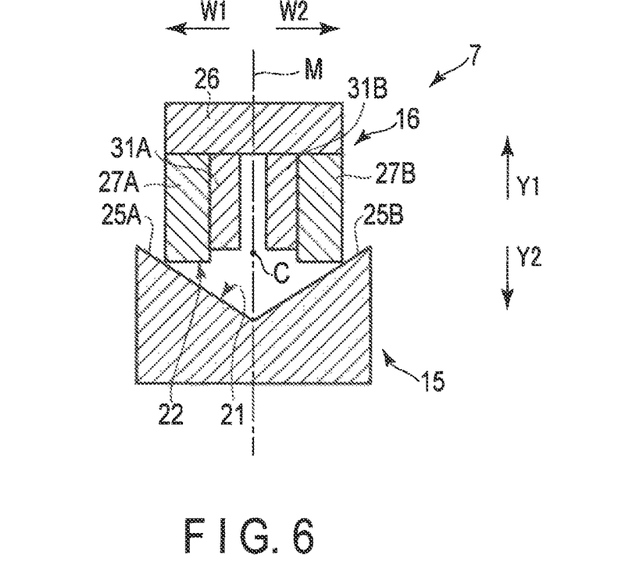
FIG. 6 is a cross-sectional view which schematically illustrates, by a cross section substantially perpendicular to the longitudinal axis, the configuration of an end effector in a state in which projection portions are not actuated by the setting in a setter according to one modification of the first embodiment.

FIG. 6 is a view illustrating the end effector 7 in a cross section substantially perpendicular to the longitudinal axis C, in a state in which the projection portions 27A and 27B are not actuated by the setting in the setter 30. As illustrated in FIG. 6, in the setting in which the projection portions 27A and 27B that are the haul portions are not actuated, restriction members 31A and 31B are disposed between the grasping pieces 15 and 16. In addition, each of the restriction members 31A and 31B interferes with (abuts on) the corresponding projection portion (corresponding one of 27A and 27B) from the inside with respect to the width direction of the end effector 7. By the interference of the corresponding restriction member (corresponding one of 31A and 31B), the bending of each of the projection portions 27A and 27B to the inside in the width direction of the end effector 7 is restricted. Thus, even when the grasping pieces 15 and 16 close relative to each other and each of the projection portions 27A and 27B is pushed and/or slid by the corresponding inclined surface (corresponding one of 25A and 25B), each of the projection portions 27A and 27B does not bend toward the inside (the central position M) in the width direction of the end effector 7. Thus, in the setting in which the projection portions 27A and 27B are not actuated, the blood vessel (treated target), which is grasped between the grasping pieces 15 and 16, is not hauled.

On the other hand, in the setting in which the projection portions 27A and 27B are actuated, each of the restriction members 31A and 31B is disposed in such a position as to interfere with neither of the projection portions 27A and 27B. Thus, by the grasping pieces 15 and 16 being closed relative to reach other, and by each of the projection portions 27A and 27B being pushed and/or slid by the corresponding inclined surface (corresponding one of 25A and 25B), each of the projection portions 27A and 27B bends toward the inside (the central position M) in the width direction of the end effector 7. Thereby, as described above, the blood vessel (treated target), which is grasped between the grasping pieces 15 and 16, is hauled toward the inside with respect to the width direction of the end effector 7. Accordingly, in this modification, the amount of hauling of the blood vessel, which is grasped between the grasping pieces 15 and 16, varies in accordance with the switching of the actuation state of the projection portions 27A and 27B which are the haul portions (hauler).

Note that in the present embodiment, for example, a driving member (not shown), such as an electric motor, is provided in the inside of the housing 5, and the driving member is driven, for example, by the supply of electric energy from the energy control device 3. In addition, by the driving member being driven, each of the restriction members 31A and 31B moves between a position where each of the restriction members 31A and 31B interferes with the corresponding projection portion (corresponding one of 27A and 27B) (i.e. a position in the setting in which the projection portions 27A and 27B are not actuated), and a position where each of the restriction members 31A and 31B interferes with neither of the projection portions 27A and 27B (i.e. a position in the setting in which the projection portions 27A and 27B are actuated).

In the present modification, for example, in the treatment of sealing, while opening and cutting, the blood vessel of the body circulation system, the setter 30 sets the state in which the projection portions 27A and 27B are not actuated. On the other hand, for example, in the treatment of sealing, while opening and cutting, the blood vessel of the pulmonary circulation system, the setter 30 sets the state in which the projection portions 27A and 27B are actuated, and the treatment as described in the first embodiment is performed. Accordingly, in this modification, the actuation state of the projection portions 27A and 27B that are the haul portions (hauler) is switched in accordance with the kind of treated target, for example, according to whether the treated target is the blood vessel of the pulmonary circulation system or not. Thereby, the amount of hauling of the treated target by the projection portions 27A and 27B is properly adjusted in accordance with the kind of treated target.

In one modification, instead of varying the positions of the restriction members 31A and 31B, the restriction members 31A and 31B may be formed of a material such as paraffin, the rigidity of which varies by heating. In this case, in the setting in which the projection portions 27A and 27B are not actuated, the restriction members 31A and 31B are not heated and are set at normal temperatures, for example, by the control in the energy control device 3. Thus, the restriction members 31A and 31B are kept in a rigid state. Thereby, even when the grasping pieces 15 and 16 close relative to each other and each of the projection portions 27A and 27B is pushed and/or slid by the corresponding inclined surface (corresponding one of 25A and 25B), the corresponding restriction member (corresponding one of 31A and 31B) interferes, and the bend of each of the projection portions 27A and 27B is restricted. On the other hand, in the setting in which the projection portions 27A and 27B are actuated, the restriction members 31A and 31B are heated up to high temperatures, for example, by the control in the energy control device 3. Thus, the restriction members 31A and 31B are softened, and even if the corresponding restriction member (corresponding one of 31A and 31B) interferes, the bend of each of the projection portions 27A and 27B is not restricted. Accordingly, by the grasping pieces 15 and 16 being closed relative to each other, and by each of the projection portions 27A and 27B being pushed and/or slid by the corresponding inclined surface (corresponding one of 25A and 25B), each of the projection portions 27A and 27B bends toward the inside (the central portion M) in the width direction of the end effector 7. Besides, the restriction members 31A and 31B may be formed of a material such as MR (magneto-rheological) fluid, the rigidity of which varies in accordance with a generated magnetic field, or may be formed of a material the rigidity of which varies by an electric current flowing through the material.

Additionally, the setter (30), which sets the actuation state of the projection portions 27A and 27B that are the haul portions, may not be provided in the energy control device 3. In one modification, two operation buttons may be provided on the housing 5 as energy operation input portions, and these operation buttons may function as the setter (30). In this modification, by an operation input being performed by one of the operation buttons, treatment energy is applied to the treated target, and the projection portions 27A and 27B are actuated. Specifically, the state in which the projection portions 27A and 27B are actuated is set by the operation button. On the other hand, if an operation input is performed by the other of the operation buttons, treatment energy is applied to the treated target, but the projection portions 27A and 27B are not actuated. Specifically, the state in which the projection buttons 27A and 27B are not actuated is set by the operation button.

Additionally, in one example, the projection portions 27A and 27B that are the haul portions can be switched between a first actuation state and a second actuation state, based on the setting in the setter (30), and, in each of the two actuation states, each of the projection portions 27A and 27B bends toward the inside in the width direction of the end effector 7. However, in the first actuation state, the amount of bend of each of the projection portions 27A and 27B is different from that in the second actuation state. In this case, for example, in the first actuation state, compared to the second actuation state, the amount of bend of each of the projection portions 27A and 27B increases when the grasping pieces 15 and 16 are closed relative to each other, and the amount of hauling of the blood vessel (treated target) toward the inside with respect to the width direction of the end effector 7 increases.

Additionally, in the first embodiment, the first grasping piece 15 is provided with the inclined surfaces 25A and 25B, and the second grasping piece 16 is provided with the projection portions 27A and 27B. However, in one modification, the second grasping piece 16 may be provided with the inclined surfaces 25A and 25B, and the first grasping piece 15 may be provided with the projection portions 27A and 27B.

Other Embodiments, Etc.

Next, a second embodiment, which is one modification of the first embodiment, will be described with reference to FIG. 7. In the description below, the same parts as in the first embodiment are denoted by like reference numerals, and a description thereof is omitted.

Figure 7:
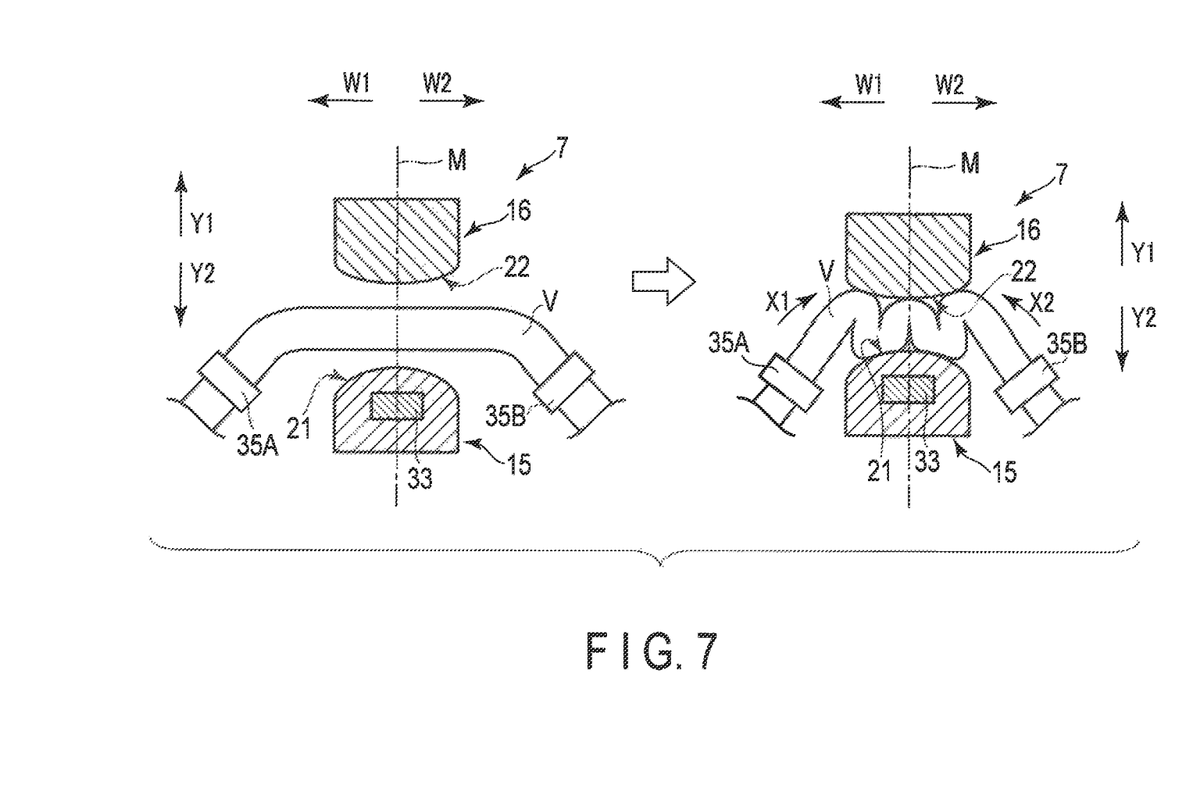
FIG. 7 is a schematic view illustrating the configuration of an end effector according to a second embodiment, and describing an operation of grasping a blood vessel between grasping pieces.

As illustrated in FIG. 7, in the present embodiment, in place of the projection portions 27A and 27B, an electromagnet 33 is provided in the first grasping piece 15 as a haul portion (hauler). In this embodiment, by an operation input being performed by the operation button 18, treatment energy is applied to the treated target that is grasped, as described above, and, at the same time, electric energy is supplied to the electromagnet 33 from the energy control device 3. By the electric energy being supplied to the electromagnet 33, the electromagnet 33 is actuated, and a magnetic field is generated in and near the end effector 7. Note that the electromagnet 33 does not need to be provided in the first grasping piece 15, and, in one modification, the electromagnet 33 may be provided in the second grasping piece 16. In another modification, electromagnets may be provided in both the grasping pieces 15 and 16.

In the treatment of coagulating, while cutting and opening, the blood vessel V, clips 35A and 35B are attached to the blood vessel V. The clips 35A and 35B are formed of a magnetic material such as stainless, and are disposed on the outside relative to the end effector 7 in the width direction (directions of arrow W1 and arrow W2) of the end effector 7. Here, the clip 35A is disposed apart from the end effector 7 on one side (arrow W1 side) of the width direction, and the clip 35B is disposed apart from the end effector 7 on the other side (arrow W2 side) of the width direction.

When the grasping pieces 15 and 16 close relative to each other in the state in which the blood vessel (treated target) V is disposed between the grasping pieces 15 and 16, a magnetic field is generated by the actuation of the electromagnet 33, and thereby magnetic force acts on the clips 35A and 35B. By the magnetic force, each of the clips 35A and 35B moves toward the inside in the width direction of the end effector 7 (grasping pieces 15 and 16). By the movement of the clips 35A and 35B, the blood vessel V is hauled toward the inside (the central position M) with respect to the width direction of the end effector 7, as indicated by arrow X1 and arrow X2. Specifically, when the grasping pieces 15 and 16 close relative to each other, the electromagnet 33 that is the haul portion (hauler) is actuated, and thereby the blood vessel V is hauled from the region located on the outside relative to the grasping pieces 15 and 16 in the width direction of the end effector 7 toward the region between the grasping pieces 15 and 16 (between the opposed surfaces 21 and 22). Thus, in this embodiment, too, the energy treatment instrument 2, which has the same function and advantageous effects as in the first embodiment and is suitable for the treatment of sealing, while cutting and opening, the blood vessel of the pulmonary circulation system, can be provided. Specifically, in this embodiment, too, there can be provided the energy treatment instrument 2 which can exhibit the proper treatment performance even when the compositions of biological tissues are different, for example, as in the case in which the compositions of biological tissues are different between the blood vessel of the pulmonary circulation system and the blood vessel of the body circulation system.

In one embodiment of the second embodiment, the above-described setter (30), which sets the actuation state of the electromagnet 33 that is the haul portion, may be provided in the energy control device 3 or housing 5. In this case, for example, in the setting in which the electromagnet 33 is not actuated, electric energy is not supplied to the electromagnet 33, and the magnetic field by the electromagnet 33 is not generated. Thus, the treated target is not hauled. On the other hand, in the setting in which the electromagnet 33 is actuated, the magnetic field is generated by the electromagnet 33, and the treated target is hauled as described above.

In another modification, the actuation state of the electromagnet 33 may be switched by adjusting, based on the setting in the setter (30), the magnitude of electric energy which is supplied to the electromagnet 33. In this case, in accordance with the switching of the actuation state of the electromagnet 33, the magnitude of the magnetic field generated by the electromagnet 33 varies, and the amount of hauling of the treated target varies.

Next, a third embodiment, which is one modification of the first embodiment, will be described with reference to FIG. 8. In the description below, the same parts as in the first embodiment are denoted by like reference numerals, and a description thereof is omitted.

Figure 8:
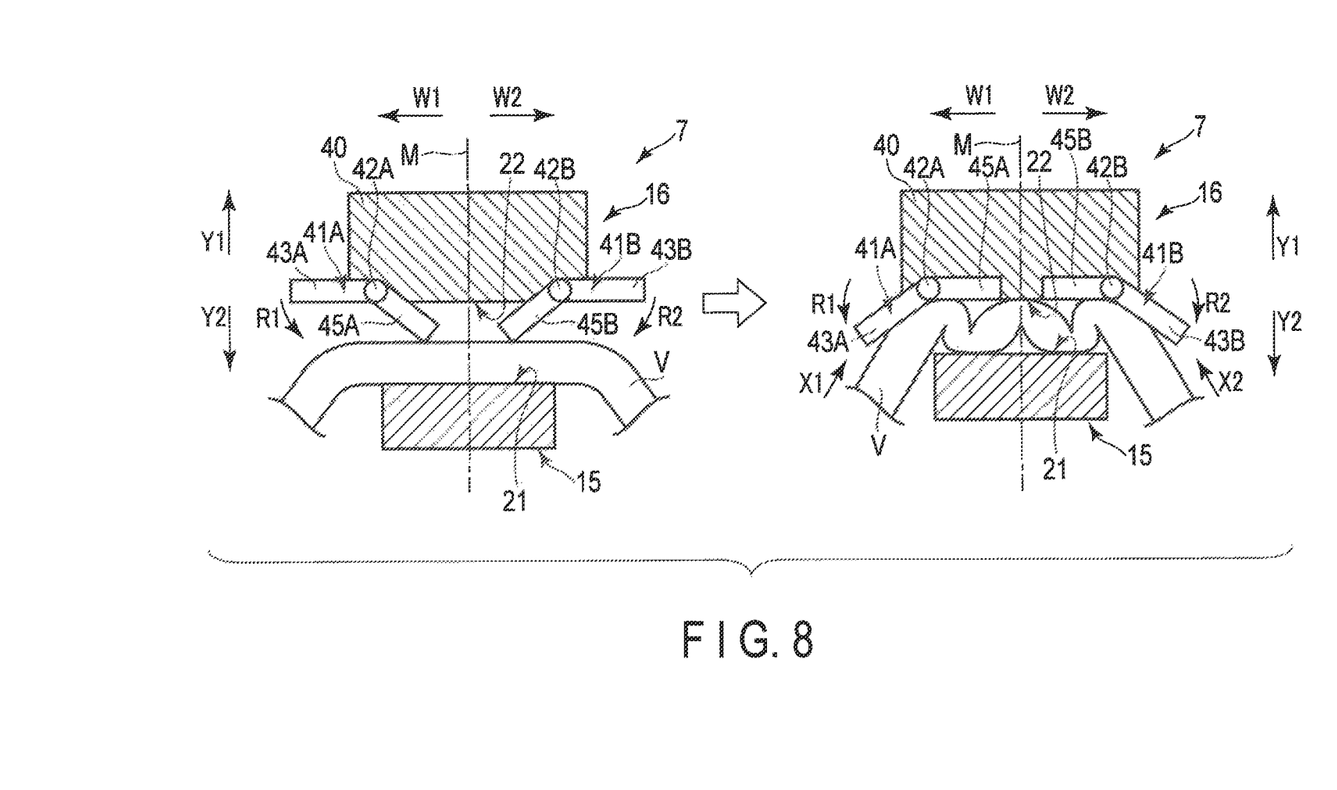
FIG. 8 is a schematic view illustrating the configuration of an end effector according to a third embodiment, and describing an operation of grasping a blood vessel between grasping pieces.

As illustrated in FIG. 8, in the present embodiment, in place of the projection portions 27A and 27B, rotary members 41A and 41B are provided in the second grasping piece 16 as haul portions (hauler). In this embodiment, the second grasping piece 16 includes a base portion 40. The rotary member 41A is attached to the base portion 40 via a support shaft 42A, and the rotary member 41B is attached to the base portion 40 via a support shaft 42B. Each of the rotary members 41A and 41B can rotate relative to the base portion 40 about the corresponding support shaft (corresponding one of 42A and 42B). Note that the extending direction of each of the support shafts 42A and 42B (i.e. the extending direction of the rotational axis of each of the rotary members 41A and 41B) is substantially parallel to the extending direction of the second grasping piece 16, and crosses (is substantially perpendicular to) the width direction of the end effector 7.

In the present embodiment, the rotary member 41A is located on one side (arrow W1 side) of the width direction (the directions of arrow W1 and arrow W2) of the second grasping piece 16 with respect to the central position M in the width direction of the second grasping piece 16, and the rotary member 41B is located on the other side (arrow W2 side) of the width direction with respect to the central position M. In addition, the rotary member 41A includes link portions 43A and 45A, and the rotary member 41B includes link portions 43B and 45B. Incidentally, the rotary members 41A and 41B do not need to be provided in the second grasping piece 16. In one modification, the first grasping piece 15 may be provided with the same structure as the rotary members (41A and 41B). In another modification, both the grasping pieces 15 and 16 may be provided with the same structure as the rotary members (41A and 41B).

When the grasping pieces 15 and 16 close relative to each other in the state in which the blood vessel (treated target) V is disposed between the grasping pieces 15 and 16, the link portion 45A of the rotary member 41A and the link portion 45B of the rotary member 41B are pushed by the blood vessel V and the first grasping piece 15. At this time, the link portions 45A and 45B are pushed toward the side (arrow Y1 side) toward which the second grasping piece 16 opens. By the link portion 45A being pushed, the rotary member 41A rotates to an arrow R1 side around the support shaft 42A. By the rotation of the rotary member 41A, the link portion 43A abuts on the blood vessel V, and the link portion 43A pushes the blood vessel V toward the inside in the width direction of the end effector 7. Similarly, by the link portion 45B being pushed, the rotary member 41B rotates to an arrow R2 side around the support shaft 42B. By the rotation of the rotary member 41B, the link portion 43B abuts on the blood vessel V, and the link portion 43B pushes the blood vessel V toward the inside in the width direction of the end effector 7.

As described above, by each of the rotary members 41A and 41B being actuated, the blood vessel V is pushed by each of the rotating rotary members 41A and 41B toward the inside in the width direction of the end effector 7. Thereby, as indicated by arrow X1 and arrow X2, the blood vessel V is hauled toward the inside (the central position M) with respect to the width direction of the end effector 7. Specifically, when the grasping pieces 15 and 16 close relative to each other, the rotary members 41A and 41B that are the haul portions are actuated, and thereby the blood vessel V is hauled from the region located on the outside relative to the grasping pieces 15 and 16 in the width direction of the end effector 7 toward the region between the grasping pieces 15 and 16 (between the opposed surfaces 21 and 22). Thus, in this embodiment, too, the energy treatment instrument 2, which has the same function and advantageous effects as in the first embodiment and is suitable for the treatment of sealing, while cutting and opening, the blood vessel of the pulmonary circulation system, can be provided. Specifically, in this embodiment, too, there can be provided the energy treatment instrument 2 which can exhibit the proper treatment performance even when the compositions of biological tissues are different, for example, as in the case in which the compositions of biological tissues are different between the blood vessel of the pulmonary circulation system and the blood vessel of the body circulation system.

In one modification of the third embodiment, the above-described setter (30), which sets the actuation state of the rotary members 41A and 41B that are the haul portions, may be provided in the energy control device 3 or housing 5. In this case, for example, in the setting in which the rotary members 41A and 41B are not actuated, the rotational movement of each of the rotary members 41A and 41B is restricted by a restriction member such as a stopper, and the rotary members 41A and 41B are set in an unrotatable state. Thus, the treated target is not hauled. On the other hand, in the setting in which the rotary members 41A and 41B are actuated, the restriction member interferes with neither of the rotary members 41A and 41B, and the rotational movement of the rotary members 41 and 41B is not restricted. Thus, the treated target is hauled as described above.

In another modification, the actuation state of the rotary members 41A and 41B may be switched based on the setting in the setter (30), and thereby the magnitude of the range of rotational movement of each of the rotary members 41A and 41B may be varied. In this case, since the magnitude of the range of rotational movement of each of the rotary members 41A and 41B varies, the amount of hauling of the treated target varies in accordance with the switching of the actuation state of each rotary member 41A, 41B.

Next, a fourth embodiment, which is one modification of the first embodiment, will be described with reference to FIG. 9. In the description below, the same parts as in the first embodiment are denoted by like reference numerals, and a description thereof is omitted.

Figure 9:
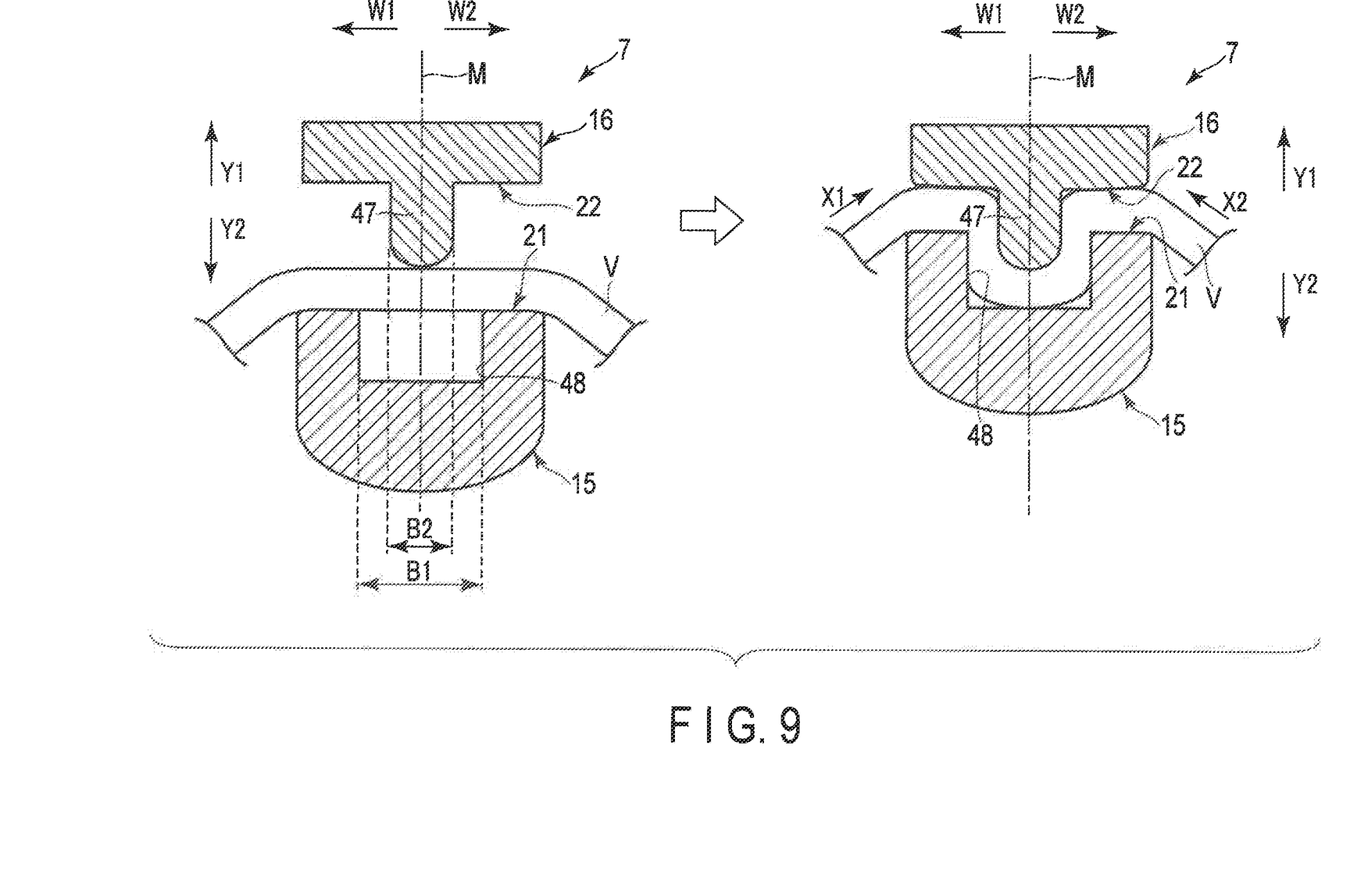
FIG. 9 is a schematic view illustrating the configuration of an end effector according to a fourth embodiment, and describing an operation of grasping a blood vessel between grasping pieces.

As illustrated in FIG. 9, in the present embodiment, in place of the projection portions 27A and 27B, a projection 47 and a recess portion 48 are provided in the end effector 7 as haul portions (hauler). In this embodiment, the projection 47 is provided on the second opposed surface 22 of the second grasping piece 16. The projection 47 projects toward the first grasping piece side (arrow Y2 side), compared to the other part of the second opposed surface 22. In addition, the recess portion 48 is provided on the first opposed surface 21 of the first grasping piece 15. Compared to the other part of the first opposed surface 21, the recess portion 48 is recessed toward the side (arrow Y2 side) toward which the first grasping piece 15 opens. Note that in one modification, the projection (47) may be provided on the first grasping piece 15, and the recess portion (48) may be provided on the second grasping piece 16.

The central position M in the width direction of the end effector 7 passes through the projection 47 and recess portion 48. In addition, a dimension B1 of the recess portion 48 in the width direction of the end effector 7 is greater than a dimension B2 of the projection 47 in the width direction of the end effector 7. In the state in which the grasping pieces 15 and 16 close relative to each other, the projection 47 is inserted in the recess portion 48.

When the grasping pieces 15 and 16 close relative to each other in the state in which the blood vessel (treated target) V is disposed between the grasping pieces 15 and 16, the projection 47 is inserted in the recess portion 48. Thus, the blood vessel V is pushed toward the inside of the recess portion 48 by the projection 47. Specifically, by the projection 47 and recess portion 48 being actuated, the blood vessel V is inserted in the recess portion 48 by the pushing from the projection 47. By the blood vessel V being inserted in the inside of the recess portion 48, the blood vessel V is hauled toward the inside (the central position M) in the width direction of the end effector 7, as indicated by arrow X1 and arrow X2. Specifically, when the grasping pieces 15 and 16 close relative to each other, the projection 47 and recess portion 48 that are the haul portions are actuated, and thereby the blood vessel V is hauled from the region located on the outside of the grasping pieces 15 and 16 in the width direction of the end effector 7 toward the region between the grasping pieces 15 and 16 (between the opposed surfaces 21 and 22). Thus, even in the case of the blood vessel of the pulmonary circulation system in which the amount of the biological high polymer in the cross section perpendicular to the extending direction is small, the length (volume) of the portion clamped between the grasping pieces 15 and 16 increases in the range of the width B1. Therefore, a sufficient amount of biological high polymer is secured in the entirety of the portion clamped between the grasping pieces 15 and 16 in the blood vessel. Thus, in this embodiment, too, the energy treatment instrument 2, which has the same function and advantageous effects as in the first embodiment and is suitable for the treatment of sealing, while cutting and opening, the blood vessel of the pulmonary circulation system, can be provided. Specifically, in this embodiment, too, there can be provided the energy treatment instrument 2 which can exhibit the proper treatment performance even when the compositions of biological tissues are different, for example, as in the case in which the compositions of biological tissues are different between the blood vessel of the pulmonary circulation system and the blood vessel of the body circulation system.

In the above-described embodiments, etc., the energy treatment instrument (2) includes the first grasping piece (15), and the second grasping piece (16) which openable and closeable relative to the first grasping piece (15), and which can grasp the treated target between the second grasping piece (16) and the first grasping piece (15) by closing relative to the first grasping piece (15). At least one of the first grasping piece (15) and second grasping piece (16) includes the energy applying portion (21; 22; 21, 22) which treats the treated target by applying treatment energy to the treated target grasped between the first grasping piece (15) and second grasping piece (16). At least one of the first grasping piece (15) and second grasping piece (16) includes the haul portion (27A, 27B; 33; 41A, 41B; 47, 48) which hauls the treated target toward the inside in the width direction (W1, W2) of the first grasping piece (15) and second grasping piece (16), when the first grasping piece (15) and second grasping piece (16) close relative to each other in the state in which the treated target is disposed between the first grasping piece (15) and second grasping piece (16).

Hereafter, characteristic items will be additionally described.

(Additional item 1)

A treatment method comprising:

closing a first grasping piece and a second grasping piece relative to each other, and grasping a treated target between the first grasping piece and the second grasping piece;

hauling the treated target, which is grasped between the first grasping piece and the second grasping piece, toward an inside in a width direction of the first grasping piece and the second grasping piece, when the first grasping piece and the second grasping piece close relative to each other; and applying treatment energy to the treated target hauled to a region between the first grasping piece and the second grasping piece, and sealing the treated target.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy treatment instrument comprising:
a first grasping piece;
a second grasping piece openable and closable relative to the first grasping piece, the second grasping piece being configured to grasp a treated target between the second grasping piece and the first grasping piece by closing relative to the first grasping piece;
an energy applying surface provided in at least one of the first grasping piece and the second grasping piece, the energy applying surface being configured to treat the treated target by applying treatment energy to the treated target grasped between the first grasping piece and the second grasping piece; and
a hauler provided in at least one of the first grasping piece and the second grasping piece, the hauler being configured to haul the treated target toward an inside in a width direction of the first grasping piece and the second grasping piece, when the first grasping piece and the second grasping piece close relative to each other in a state in which the treated target is disposed between the first grasping piece and the second grasping piece, the hauler including:
a first projection portion and a second projection portion separated from the first projection portion, and
a first inclined surface opposed to the first projection portion, and a second inclined surface opposed to the second projection portion on surfaces opposed to the first projection portion and the second projection portion, the first inclined surface and the second inclined surface forming a recess with a bottom having a greatest depth at a center of the recess in a width direction of the hauler, the first projection portion and the second projection portion deflect toward the center in the width direction by closing the first grasping piece and the second grasping piece relative to each other.

2. The energy treatment instrument of claim 1, further comprising an input device configured to set an actuation state of the hauler,
wherein the hauler is configured to vary an amount of hauling of the treated target in accordance with the actuation state based on a setting of the input device.

3. The energy treatment instrument of claim 2, wherein:
switching as to whether the hauler is actuated or not is made based on the setting of the input device, and
the treated target is not hauled based on the setting in which the hauler is not actuated, even when the first grasping piece and the second grasping piece close relative to each other.

4. An energy treatment instrument comprising:
a first grasping piece;
a second grasping piece openable and closable relative to the first grasping piece, the second grasping piece being configured to grasp a treated target between the second grasping piece and the first grasping piece by closing relative to the first grasping piece;

an energy applying surface provided in at least one of the first grasping piece and the second grasping piece, the energy applying surface being configured to treat the treated target by applying treatment energy to the treated target grasped between the first grasping piece and the second grasping piece;

a hauler provided in at least one of the first grasping piece and the second grasping piece, the hauler being configured to haul the treated target toward an inside in a width direction of the first grasping piece and the second grasping piece, when the first grasping piece and the second grasping piece close relative to each other in a state in which the treated target is disposed between the first grasping piece and the second grasping piece;

a plurality of stoppers; and an input device configured to set an actuation state of the hauler, wherein:

the first grasping piece includes a first opposed surface which is opposed to the second grasping piece, the first opposed surface includes a first inclined surface and a second inclined surface, the first inclined surface and the second inclined surface extending toward a direction of opening of the first grasping piece while extending toward an inside in the width direction in a cross section perpendicular to a longitudinal direction, the hauler includes a first projection portion projecting toward the first grasping piece, and a second projection portion provided apart from the first projection portion in the width direction, the second projection portion projecting toward the first grasping piece, the hauler is configured to vary an amount of hauling of the treated target in accordance with the actuation state based on a setting of the input device, each of the plurality of stoppers are disposed in an inside of a corresponding one of the first projection portion and the second projection portion in the width direction of the first grasping piece and the second grasping piece, and the input device is configured to switch the plurality of stoppers between a first position and a second position, each of the plurality of stoppers abutting on the corresponding one of the first projection portion and the second projection portion in the first position, and each of the plurality of stoppers not abutting on the first projection portion and the second projection portion in the second position.

5. The energy treatment instrument of claim 4, wherein:

switching as to whether the hauler is actuated or not is made based on the setting of the input device, and the treated target is not hauled based on the setting in which the hauler is not actuated, even when the first grasping piece and the second grasping piece close relative to each other.

6. An energy treatment system comprising:

the energy treatment instrument of claim 4; and an energy control device including a processor and a power supply configured to supply electric power to the energy treatment instrument to generate the treatment energy.

* * * * *